(12) United States Patent
Lee et al.

(10) Patent No.: US 6,514,992 B1
(45) Date of Patent: Feb. 4, 2003

(54) CASPASES AND APOPTOSIS

(75) Inventors: Dennis Lee, San Mateo, CA (US); Scott A. Long, Ballwin, MO (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/719,724

(22) PCT Filed: Jun. 18, 1999

(86) PCT No.: PCT/US99/13748

§ 371 (c)(1),
(2), (4) Date: Dec. 14, 2000

(87) PCT Pub. No.: WO99/65451

PCT Pub. Date: Dec. 23, 1999

Related U.S. Application Data

(60) Provisional application No. 60/089,723, filed on Jun. 18, 1998.

(51) Int. Cl.$^7$ .............................................. A61K 31/445
(52) U.S. Cl. ...................... 514/323; 514/329; 514/339; 514/418
(58) Field of Search ................................ 514/329, 418, 514/339, 323

(56) References Cited

U.S. PATENT DOCUMENTS

| 4,966,901 A | 10/1990 | Zoller, et al. ................ 514/211 |
| 5,169,856 A | 12/1992 | Goto et al. .................. 514/331 |

*Primary Examiner*—Dwayne C. Jones
(74) *Attorney, Agent, or Firm*—Loretta J. Henderson; Mary E. McCarthy; Charles M. Kinzig

(57) ABSTRACT

The present invention is to novel compounds of Formula (I), their pharmaceutical compositions, and to the novel inhibition of Caspases for use in the treatment of apoptosis, and disease states caused by excessive or inappropriate cell death.

20 Claims, No Drawings

CASPASES AND APOPTOSIS

CONTINUING DATA

This application is a 371 of PCT/US99/13748, filed on Jun. 18, 1999, and claims the benefit of provisional application No. 60/089,723, filed Jun. 18, 1998.

FIELD OF THE INVENTION

The present invention is to the discovery of a new method to block excessive or inappropriate apoptosis in a mammal.

BACKGROUND

It has been recognized for over a century that there are different forms of cell death. One form of cell death, necrosis, is usually the result of severe trauma and is a process that involves loss of membrane integrity and uncontrolled release of cellular contents, often giving rise to inflammatory responses. In contrast, apoptosis is a more physiological process that occurs in a controlled manner and is generally non-inflammatory in nature. For this reason apoptosis is often referred to as programmed cell death. The name itself (apoptosis: Greek for "dropping off", for example leaves from trees) implies a cell death that is part of a normal physiological process (Kerr et al., *Br. J. Cancer,* 26: 239–257 (1972)).

Apoptosis appears to be a carefully controlled series of cellular events which ultimately leads to death of the cell. This process for elimination of unwanted cells is active and requires expenditure of cellular energy. The morphological characteristics of apoptosis include cell shrinkage and loss of cell-cell contact, condensation of nuclear chromatin followed by fragmentation, the appearance of membrane ruffling, membrane blebbing and apoptotic bodies. At the end of the process, neighboring cells and macrophages phagocytose the fragments from the apoptotic cell. The process can be very fast, occurring in as little as a few hours (Bright et al., *Biosci. Rep.,* 14: 67–82 (1994)).

The best defined biochemical event of apoptosis involves the orderly destruction of nuclear DNA. Signals for apoptosis promote the activation of specific calcium- and magnesium-dependent endonucleoases that cleave the double stranded DNA at linker regions between nucleosomes. This results in production of DNA fragments that are multiples of 180–200 base pair fragments (Bergamaschi et al., *Haematologica,* 79: 86–93 (1994); Stewart, *JNCI,* 86: 1286–1296 (1994)). When examined by agarose gel electrophoresis, these multiple fragments form a ladder pattern that is characteristic for most cells undergoing apoptosis.

There are numerous stimuli that can signal cells to initiate or promote cellular apoptosis, and these can be different in different cells. These stimuli can include glucocorticoids, TNFa, growth factor deprivation, some viral proteins, radiation and anticancer drugs. Some of these stimuli can induce their signals through a variety of cell surface receptors, such as the TNF/nerve growth factor family of receptors, which include CD40 and Fas/Apo-1 (Bright et al., supra). Given this diversity in stimuli that cause apoptosis it has been difficult to map out the signal transduction pathways and molecular factors involved in apoptosis. However, there is evidence for specific molecules being involved in apoptosis.

The best evidence for specific molecules that are essential for apoptosis comes from the study of the nematode *C. elegans.* In this system, genes that appear to be required for induction of apoptosis are Ced-3 and Ced-4. These genes must function in the dying cells and, if either gene is inactivated by mutation, cell death fails to occur (Yuan et al., *Devel. Biol.,* 138: 33–41 (1990)). In mammals, genes that have been linked with induction of apoptosis include the proto-oncogene c-myc and the tumor suppresser gene p53 (Bright et al., supra; Symonds et al., *Cell,* 78: 703–711 (1994)).

In this critical determination of whether or not to undergo apoptosis, it is not surprising that these are genes that program for proteins that inhibit apoptosis. An example in *C. elegans* is Ced-9. When it is abnormally activated, cells survive that would normally die and, conversely, when Ced-9 is inactivated cells die that would normally live (Stewart, B. W., supra). A mammalian counterpart is bcl-2, which had been identified as a cancer-causing oncogene. This gene inhibits apoptosis when its product is overexpressed in a variety of mammalian cells, rendering them less sensitive to radiation, cytotoxic drugs and apoptotic signals such as c-myc (Bright et al., supra). Some virus protein have taken advantage of this ability of specific proteins to block apoptosis by producing homologous viral proteins with analogous functions. An example of such a situation is a protein produced by the Epstein Barr virus that is similar to bcl-2, which prevents cell death and thus enhances viral production (Wells et al., *J. Reprod. Fertil.,* 101: 385–391 (1994)). In contrast, some proteins may bind to and inhibit the function of bcl-2 protein, an example being the protein bax (Stewart, B. W., supra). The overall picture that has developed is that entry into apoptosis is regulated by a careful balancing act between specific gene products that promote or inhibit apoptosis (Barinaga, *Science,* 263: 754–756 (1994)).

Apoptosis is an important part of normal physiology. The two most often sited examples of this are fetal development and immune cell development. In development of the fetal nervous system, over half of the neurons that exist in the early fetus are lost by apoptosis during development to form the mature brain (Bergamaschi et al., *Haematologica,* 79: 86–93 (1994)). In the production of immune competent T cells (and to a lesser extent evidence exists for B cells), a selection process occurs that eliminates cells that recognize and react against self. This selection process is thought to occur in an apoptotic manner within areas of immune cell maturation (Williams, G. T., *J. Pathol.,* 173: 1–4 (1994); Krammer et al., *Curr. Opin. Immunol.,* 6: 279–289 (1994)).

Dysregulation of apoptosis can play an important role in disease states, and diseases can be caused by both excessive or too little apoptosis occurring. An example of diseases associated with too little apoptosis would be certain cancers. There is a follicular B-cell lymphoma associated with an aberrant expression of functional bcl-2 and an inhibition of apoptosis in that cell (Bergamaschi et al., supra). There are numerous reports that associate deletion or mutation of p53 with the inhibition of apoptosis and the production of cancerous cells (Kerr et al., *Cancer,* 73: 2013–2026 (1994); Ashwell et al., *Immunol. Today,* 15: 147–151, (1994)). In contrast, one example of excessive or inappropriate apoptosis is the loss of neuronal cells that occurs in Alzheimer disease, possible induced by bamyloid peptides (Barr et al., *BioTechnology,* 12: 487–493 (1994)). Other examples include excessive apoptosis of $CD4^+$ T cells that occurs in HIV infection, of cardiac myocytes during infarction/reperfusion and of neuronal cells during ischemia (Bergamaschi et al., supra); Barr et al., supra).

Some pharmacological agents attempt to counteract the lack of apoptosis that is observed in cancers. Examples include topoisomerase II inhibitors, such as the epipodophyllotoxins, and antimetabolites, such as ara-c, which have been reported to enhance apoptosis in cancer cells (Ashwell et al., supra). In many cases with these anti-cancer drugs, the exact mechanism for the induction of apoptosis remains to be elucidated.

In the last few years, evidence has built that ICE and proteins homologous to ICE (Caspases) play a key role in apoptosis. This area of research has been spurred by the observation of homology between the protein coded by Ced-3, a gene known to be critical for *C. Elegans* apoptosis, and ICE (Caspase 1). These two proteins share 29% amino acid identity, and complete identity in the 5 amino acid portion thought to be responsible for protease activity (QACRG) (Yuan et al., *Cell*, 75: 641–652 (1993)). Additional homologies are observed between ICE and the product of the nedd-2 gene in mice, a gene suspected of involvement in apoptosis in the developing brain (Kumar et al., *Genes Dev.*, 8: 1613–1626 (1994)) and Ich-1 (Caspase 2) and CPP32 (Caspase 3), human counterparts of nedd-2 isolated from human brain cDNA libraries (Wang et al., *Cell*, 78: 739–750 (1994); Fernandes-Alnemiri et al., *J. Biol. Chem.*, 269: 30761–30764 (1994)).

Further proof for the role of these proteins in apoptosis comes from transfection studies. Over expression of murine ICE caused fibroblasts to undergo programmed cell death in a transient transfection assay (Miura et al., *Cell*, 75: 653–660 (1993)). Cell death could be prevented by point mutations in the transfected gene in the region of greatest homology between ICE and Ced-3. As very strong support for the role of ICE in apoptosis, the authors showed that ICE transfection-induced apoptosis could be antagonized by overexpression of bcl-2, the mammalian oncogene that can prevent programmed cell death (Miura et al., supra). Additional experiments were performed using the crmA gene. This gene of the cowpox virus encodes a serpin protein, a family of proteins that are inhibitors of proteases (Ray et al., *Cell*, 69: 597–604 (1992)). Specifically, the protein of crmA has been shown to inhibit processing of pro-interleukin-1b by ICE. (Gagliardini et al. *Science*, 263: 826–828 (1994)) showed that microinjection of the crmA gene into dorsal root ganglion neurons prevented cell death induced by nerve growth factor deprivation. This result shows that ICE is involved in neuronal cell apoptosis. A more direct demonstration of ICE involvement comes from experiments in which ICE transfection is coupled with the co-expression of crmA, demonstrating a crmA-induced suppression of the ICE-induced apoptosis response (Miura et al., supra; Wang et al., supra).

In addition to ICE, researchers have examined the ability of Caspases to promote apoptosis. (Kumar et al. supra) demonstrated that over expression of nedd-2 in fibroblasts and neuroblastoma cells resulted in cell death by apoptosis and that this apoptosis could also be suppressed by expression of the bcl-2 gene. Most recently, Wang et al., (Wang et al., supra) examined the over expression of Ich-1 in a number of mammalian cells. Expression resulted in cell apoptosis, which could be antagonized by bcl-2 coexpression. Mutation of a cysteine residue, contained within the QACRG motif and presumed to be critical for protease function, to serine abolished apoptotic activity.

Further evidence for a role of a cysteine protease in apoptosis comes from a recent report by Lazebnik et al. (*Nature*, 371: 346–347 (1994)). These authors have used a cell-free system to mimic and study apoptosis. In their system there is a protease activity that cleaves the enzyme poly(ADP-ribose) polymerase at a site identical to a cleavage site in pre-interleukin-1b. However, this yet to be isolated protease and ICE appear to be different and to act on different substrate proteins. Blockade of protease activity in the system, using non-selective cysteine protease inhibitors, resulted in inhibition of apoptosis.

Taken together, the above evidence provides striking involvement of Caspases in the induction of apoptosis in mammalian cells. Brain interleukin-1 has been reported to be elevated in Alzheimer disease and Down syndrome (Griffin et al., *Proc. Natl. Acad. Sci. U.S.A.*, 86: 7611–7615 (1989)). There are also reports that interleukin-1 can increase the mRNA and production of b-amyloid protein, a major component of senile plaques in Alzheimer disease as well as in brains of people with Down syndrome and with aging (Forloni et al., *Mol. Brain Res.*, 16: 128–134 (1992); Buxbaum et al., *Proc. Natl. Acad. Sci. U.S.A.*, 89: 10075–10078 (1992); Goldgaber et al., *Proc. Natl. Acad. Sci. U.S.A.*, 86: 7606–7610 (1989)). These reports can be viewed as additional evidence for the involvement of ICE in these diseases and the need for use of a novel therapeutic agent and therapy thereby.

To date, no useful therapeutic strategies have blocked excessive or inappropriate apoptosis. In one patent application, EPO 0 533 226 a novel peptide structure is disclosed which is said to be useful for determining the activity of ICE, and therefore useful in the diagnoses and monitoring of IL-1 mediated diseases. Therefore, a need exists to find better therapeutic agents which have non-toxic pharmacological and toxicological profiles for use in mammals. These compounds should block excessive or inappropriate apoptosis cells, and hence provide treatment for diseases and conditions in which this condition appears.

SUMMARY OF THE INVENTION

The present invention is to the novel compounds of Formula (I), their pharmaceutical compositions, and to the novel inhibition of Caspases for use in the treatment of apoptosis, and disease states caused by excessive or inappropriate cell death. The compounds of Formula I are most effective in inhibiting Caspases three and seven.

Another aspect of the present invention is to a pharmaceutical composition comprising a compound of Formula (I), or a pharmaceutically acceptable salt thereof, and a pharmaceutically acceptable carrier or diluent.

Another aspect of the present invention is to a method for the treatment of diseases or disorders associated with excessive IL-1b convertase activity, in a mammal in need thereof, which method comprises administering to said mammal an effective amount of a compound of Formula (I), or a pharmaceutically acceptable salt thereof.

Another aspect of the present invention is to a method of preventing or reducing apoptosis in a mammal, preferably a human, in need of such treatment which method comprises administering to said mammal or human an effective amount of a compound of Formula (I), or a pharmaceutically acceptable salt thereof.

Another aspect of the present invention is to a method of blocking or decreasing the production of IL-1b and/or TNF, in a mammal, preferably a human, in need of such treatment which method comprises administering to said mammal or human an effective amount of a compound of Formula (I), or a pharmaceutically acceptable salt thereof.

The compounds of Formula I are represented by the structure

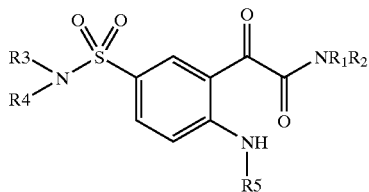

(I)

wherein
$R_1$ and $R_2$ together with the nitrogen to which they are attached form a 4 to 7 membered ring;
$R_3$ and $R_4$ together with the nitrogen to which they are attached form a 4 to 7 membered ring;
$R_5$ is

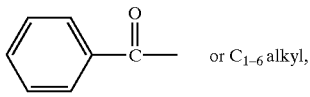

preferably methyl.

Preferably $R_1$ and $R_2$ and $R_3$ and $R_4$ are joined to form a five membered nitrogen containing ring.

Compounds exemplified by Formula (I) include, but are not limited to:

(S,S)-4-[1-(2-Methoxymethyl)pyrrolidinyl)sulfonyl]-2-[1-(2-methoxymethyl)pyrrolidino-ethanedione]-aniline
(S,S)-4-[1-(2-Phenoxymethyl)pyrrolidinyl)sulfonyl]-2-[1-(2-methoxymethyl)pyrrolidino-ethanedione]-aniline
(S,S)-4-[1-(2-(Phenoxymethyl)pyrrolidinyl)sulfonyl]-2-[1-(2-methoxymethyl)pyrrolidino-ethanedione]-N-benzoylaniline
(S,S)-4-[1-(2-(Phenoxymethyl)pyrrolidinyl)sulfonyl]-2-[1-(2-methoxymethyl)pyrrolidino-1,2-ethanedione]-N-methylaniline The term "excessive IL-1b convertase activity" is used herein to mean an excessive expression of the protein, or activation of the enzyme.

The term "$C_{1-6}$ alkyl" or "alkyl" is used herein to mean both straight and branched chain radicals of 1 to 6 carbon atoms, unless the chain length is otherwise specified, including, but not limited to, methyl, ethyl, n-propyl, iso-propyl, n-butyl, sec-butyl, iso-butyl, tert-butyl, and the like.

The present invention contains the inhibition of Caspases by compounds of Formula (I). What is meant by the term "Caspases" are fragment, homologs, analogs and derivatives of the polypeptides Interleukin-1b converting enzyme (or convertase). These analogs are structurally related to the Caspase family. They generally encode a protein (s) which exhibits high homology to the human ICE over the entire sequence. Preferably, the pentapeptide QACRG is conserved. The Caspases, which may include many natural allelic variants (such as substitutions, deletion or addition of nucleotides) does not substantially alter the function of the encoded polypeptide. That is they retain essentially the same biological function or activity as the ICE protease, although it is recognized that the biological function may be enhanced or reduced activity. The suitable activity is not IL-1b convertase activity, but the ability to induce apoptosis or involved in programmed cell death in some manner. Suitable Caspases encompasses within this invention are those described in PCT US94/07127 filed Jun. 23, 1994, and in U.S. Ser. No. 08/334,251, filed Nov. 1, 1994, whose disclosures are incorporated herein by reference in their entirety.

The term "blocking or inhibiting, or decreasing the production of IL-1b and/or TNF" as used herein refers to:

a) a decrease of excessive levels, or a down regulation, of the cytokine in a human to normal or sub-normal levels by inhibition of the in vivo release of the cytokine; or b) a down regulation, at the genomic level, of excessive in vivo levels of the cytokine (IL-1 or TNF) in a human to normal or subnormal levels; or c) a down regulation, by inhibition of the direct synthesis of the cytokine (IL-1, or TNF) as a postranslational event, or d) a down regulation, at the translational level, of excessive in vivo levels of the cytokine (IL-1, or TNF) in a human to normal or sub-normal levels.

Compound of the present invention may be synthesized in accordance with the schemes illustrated below.

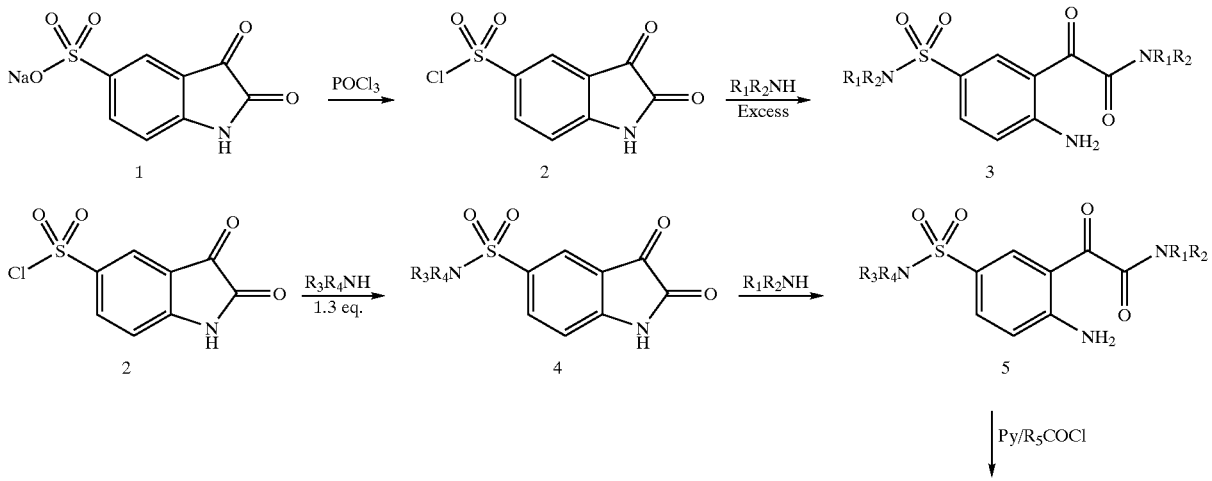

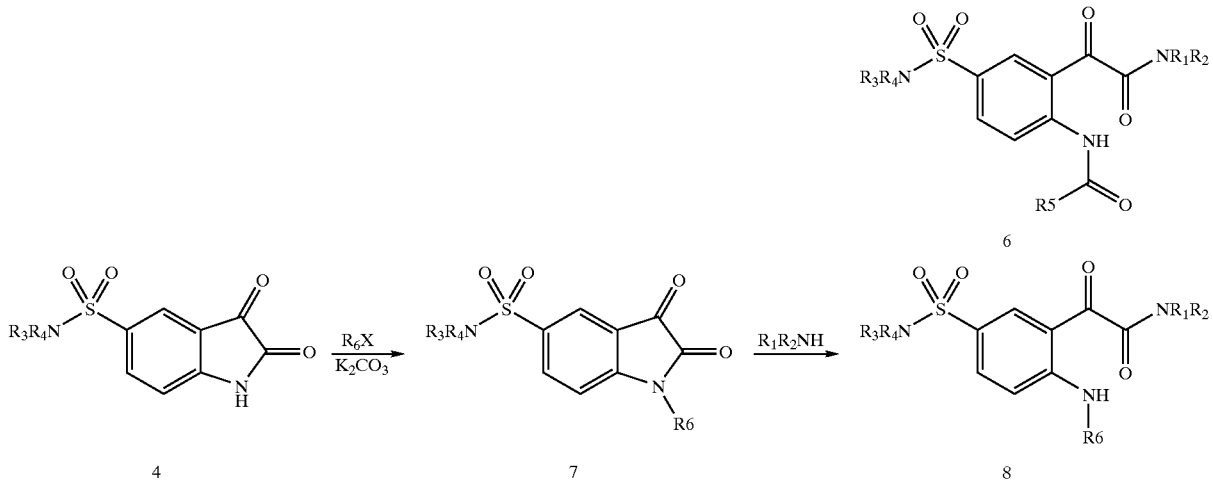

5-Isatinsulfonic acid, sodium salt (1) is treated with phosphorus oxychloride in organic solvents such as sulfolane at temperatures ranging from 50–80° C. in order to obtain 5-chlorosulfonylisatin (2) (Martinez, F; Naarmnann; H, *Synth. Met.*, 1990, 39, 195), a direct precursor to the novel compounds of this invention. Treatment of the chlorosulfonyl derivative 2 with an excess of a secondary amine in organic solvents such as tetrahydrofuran, methylene chloride or dimethylformamide yields the 4-alkylaminosulfonyl-2-alkylglyoxylamidoaniline 3. Alternatively, treatment of the chlorosulfonyl derivative 2 with a slight excess (<1.3 eq) of a secondary amine in organic solvents such as tetrahydrofuran, methylene chloride or dimethylformamide with a tertiary amine base such as triethylamine yields the 5-alkylaminosulfonylisatin 4. The 5-alkylaminosulfonylisatin derivative 4 is treated with a secondary amine base in organic solvents such as tetrahydrofuran, methylene chloride, dimethylformamide, or methanol in temperatures ranging from 25–60 ° C. to yield the 4-alkylaminosulfonyl-2-alkylglyoxylamidoaniline 5. The 4-alkylaminosulfonyl-2-alkylglyoxylamidoaniline 5 is acylated with an acyl chloride in pyridine to yield the 4-alkylaminosulfonyl-2-alkylglyoxylamido-N-acylanilide 6. Additionally, the 5-alkylaminosulfonylisatin 4 is alkylated in the presence of a base such as $K_2CO_3$ or NaH with a halide such as methyl iodide or benzyl bromide in an organic solvent to give 1-alkyl-5alkylaminosulfonlyisatin 7. The 1-alkyl-5alkylaminosulfonlyisatin 7 is treated with a secondary amine base in organic solvents such as tetrahydrofuran, methylene chloride, dimethylformamide, or methanol to yield the 4-alkylaminosulfonyl-2-alkylglyoxylamido-N-alkyl-aniline 8.

EXAMPLE 1

(S,S)-4-[1-(2-Methoxymethyl)pyrrolidinyl)sulfonyl]-2-[1-(2-methoxymethyl)pyrrolidino-ethanedione]-aniline 1a) 5-Chlorosulfonylisatin To a mixture of isatinsulfonic acid, sodium salt dihydrate (10 g, 35.1 mmol) and 50 mL tetramethylene sulfone was added phosphorus oxychloride (16.5 mL, 177 mmol). The resulting mixture was heated at 60° C. for 3 hours. The mixture was cooled to 0° C. and 120 mL of water was cautiously added. The resulting green solid was filtered and washed with water. The solid was dissolved in 100 mL EtOAc and washed thrice with 50 mL of water. The organic layer was dried over $MgSO_4$, filtered and concentrated under reduced pressure to give a yellow solid. The solid was recrystallized from EtOAc/Hexanes to give the title compound as an orange solid (5.2 g, 60.5%). ES (−) MS m/e=344 (M−H).

1b) (S,S)-4-[1-(2-Methoxymethyl)pyrrolidinyl)sulfonyl]-2-[1-(2-methoxymethyl)pyrrolidino-ethanedione]-aniline To a solution of 5-chlorosulfonylisatin (0.1 g, 0.41 mmol) in 2 mL of methylene chloride was added (S)-(+)-2-(methoxymethyl)pyrrolidine (0.14 g, 1.2 mmol) in 0.5 mL of methylene chloride. The resulting solution was stirred for 20 min and then washed with 3 N HCl. The organic layer was dried ($MgSO_4$), filtered and evaporated in vacuo to give a yellow solid. The solid was purified by silica gel flash chromatography with 1% $CH_3OH/CH_2Cl_2$ to afford the title compound as a light yellow oil (0.016 g, 9%). ES(+) MS m/e=440 (M+H).

EXAMPLE 2

(S,S)-4-[1-(2-Phenoxymethyl)pyrrolidinyl)sulfonyl]-2-[1-(2-methoxymethyl)pyrrolidino-ethanedione]-aniline 2a) (S)-(+)-N-Boc-2-(4-Toluenesulfonyloxymethyl)pyrrolidine To a solution of (S)-(+)-N-Boc-2-prolinol (3.51 g, 17.4 mmol) and pyridine (9.87 mL, 122 mmol) in 18 mL of $CH_2Cl_2$ at 0° C. was added a solution of p-toluenesulfonylchloride (3.99 g, 20.9 mmol) in 20 mL of $CH_2Cl_2$ dropwise. The solution was warmed to room temperature and stirred overnight. The solution was treated with 140 mL of water and extracted twice with 20 mL of $CH_2Cl_2$. The organic layer was then dried over $Na_2SO_4$, filtered and concentrated under reduced pressure to give an oil. The oil was purified by silica gel chromatography with 20–25% EtOAc/Hexanes to give the title compound as a colorless oil (5.6 g, 90%). ES (+) MS m/e=256 (M+H).

2b) (S)-(+)-N-Boc-2-Phenoxymethylpyrrolidine

To a solution of phenol (0.40 g, 4.23 mmol) in 10 mL of THF at 0° C. was added sodium hydride (0.226 g, 5.65 mmol), and the mixture was warmed to room temperature. The mixture was stirred 10 minutes (until evolution of hydrogen gas ceased) and cooled to 0° C. A solution of (S)-(+)-N-Boc-2-(4-toluenesulfonyloxymethyl)pyrrolidine (1.0 g, 2.8 mmol) in 2 mL of THF was added dropwise and the resulting mixture was refluxed overnight. To the mixture was added 5 mL of DMF and the mixture was heated at 100° C. overnight. To the mixture was added EtOAc and the organic layer was washed thrice with water, thrice with 1N NaOH, and twice with water. The organic layer was then dried over $MgSO_4$, filtered and concentrated under reduced pressure to give an oil. The oil was purified by silica gel chromatography with 7% EtOAc/Hexanes to give the title compound as a colorless oil (0.55 g, 71%). ES (+) MS m/e=278 (M+H).

2c) (S)-(+)-2-Phenoxymethylpyrrolidine

To a solution of (S)-(+)-N-Boc-2-phenoxymethylpyrrolidine (0.81 g, 2.9 mmol) in 5 mL of $CH_2Cl_2$ at 0° C. was added 5 mL of TFA dropwise over 1 hour. The solution was warmed to room temperature and stirred for 1.5 hours. The reaction mixture was slowly poured into 30 mL of 10% NaOH and extracted thrice with 20 mL of $CH_2Cl_2$. The organic layer was then dried over $Na_2SO_4$, filtered and concentrated under reduced pressure to give a light yellow oil (0.41 g, 79%). ES (+) MS m/e=178 (M+H).

2d) (S)-(+)-5-[1-(2-Phenoxymethylpyrrolidinyl) sulfonyl]isatin

To a solution of 5-chlorosulfonylisatin (0.2 g, 0.82 mmol) in 8 mL of 1:1 $THF:CHCl_3$ at 0° C. was added dropwise, via syringe pump, a solution of (S)-(+)-2-phenoxymethylpysrolidine (0.19 g, 1.1 mmol) and N,N-diisopropylethylamine (0.21 g, 1.6 mmol) in 1 mL of $CHCl_3$. The reaction was followed by TLC until complete (about 20 min). The solution was concentrated under reduced pressure to a small volume and purified by silica gel chromatography with 2% $CH_3OH/CH_2Cl_2$ to give an orange solid. The solid was then recrystallized from EtOAc/Hexanes to give the title compound as an orange solid (0.15 g, 47%). ES (+) MS m/e=387 (M+H).

2e) (S,S)-4-[1-(2-Phenoxymethyl)pyrrolidinyl) sulfonyl]-2-[1-(2-methoxymethyl)pyrrolidino-ethanedione]-aniline To a solution of (S)-(+)-5-[1-(2-phenoxymethyl) pyrrolidinyl)sulfonyl]isatin (0.051 g, 0.13 mmol) in 1.0 mL of methanol was added (S)-(+)-2-(methoxymethyl) pyrrolidine (0.051 g, 0.40 mmol) in 0.5 mL of methanol. The resulting solution was heated at 55° C. for 3 h. The solution was evaporated in vacuo and the resulting oil was purified by silica gel flash chromatography with 2% $CH_3OH/CH_2Cl_2$ to afford an oil. This oil was then further purified by MPLC with 40% EtOAc/Hexanes to afford the title compound as a yellow oil (0.053 g, 80%). ES (+) MS m/e=502 (M+H).

EXAMPLE 3

(S,S)-4-[1-(2-(Phenoxymethyl)pyrrolidinyl) sulfonyl]-2-[1-(2-methoxymethyl)pyrrolidino-ethanedione]-N-benzoylaniline To a solution of (S,S)-4-[1-(2-phenoxymethyl) pyrrolidinyl)sulfonyl]-2-[1-(2-methoxymethyl)pyrrolidino-ethanedione]-aniline (0.011 g, 0.023 mmol) in 0.2 mL of pyridine was added benzoyl chloride (0.004 mL, 0.034 mmol) and the resulting solution was stirred overnight. Excess benzoyl chloride (0.05 mL, 0.43 mmol) was added and the solution was stirred for 3 h. The solution was then washed with 3 N HCl and extracted twice with EtOAc. The organic layer was dried ($MgSO_4$), filtered and evaporated in vacuo to give an oil. The oil was purified by silica gel flash chromatography with 30% EtOAc/Hexanes to afford the title compound as a colorless oil (0.010 g, 74%). ES (+) MS m/e=606 (M+H).

EXAMPLE 4

(S,S)-4-[1-(2-(Phenoxymethyl)pyrrolidinyl) sulfonyl]-2-[1-(2-methoxymethyl)pyrrolidino-1,2-ethanedione]-N-methylaniline 4a) (S)-1-methyl-5-[1-(2-(Phenoxymethyl) pyrrolidinyl)sulfonyl]isatin To a mixture of (S)-(+)-5-[1-(2-Phenoxymethyl) pyrrolidinyl)sulfonyl]isatin (0.20 g, 0.52 mmol) and potassium carbonate (0.18 g, 1.30 mmol) in 2 mL of DMF was added methyl iodide (0.048 mL, 0.78 mmol). The resulting mixture was stirred for 18 h. Ethyl acetate was added to the reaction mixture and it was washed with water. The organic layer was dried ($MgSO_4$), filtered and evaporated in vacuo to give an orange solid. The solid was purified by silica get flash chromatography with 1% $CH_3OH/CH_2Cl_2$ to afford the title compound a s a yellow solid (0.019 g, 90%). ES (+) MS m/e 823 (2M+Na).

4b) (S,S)-4-[1-(2-(Phenoxymethyl)pyrrolidinyl) sulfonyl]-2-[1-(2-methoxymethyl)pyrrolidino-1,2-ethanedione]-N-methylaniline To a solution of (S)-1-methyl-5-[1-(2-(Phenoxymethyl) pyrrolidinyl)sulfonyl]isatin (0.050 g, 0.125 mmol) in 2.5 mL of THF was added (S)-(+)-2-(methoxymethyl)pyrrolidine (0.125 mL, 1.01 mmol). The resulting solution was stirred for 18 h. A solution of 3N HCL was added and the mixture was extracted twice with Ethyl acetate. The organic layer was dried ($Na_2SO_4$), filtered and evaporated in vacuo to give an oil. The oil was purified by silica gel MPLC with 40% EtOAc/Hexanes to afford the title compound as a light yellow foam (0.048 g, 75%). ES (+) MS m/e=516 (M+H).

Preparation of Active Caspase 3

Full length aspase 3 was ex pressed intracellularly in E.coli with N-terminal hexa His tag. *E coli* cells were lysed in 10 ml/g of cells of lysis buffer (50 mM Na phosphate pH 7.2, 0.1 M NaCl, 0.1% Tween 20, and 10 mM b-mercaptoethanol) using Microfluidics M110Y homogenizer at 10,000 psi. After centrifugation, Caspase 3 activity was detected in lysate supernatant. Th e supernatant was buffer-exchanged on Sephadex G25 column equilibrated with 20 mM TrisHCl, 10% Sucrose, 0.1% CHAPS, 2 mM DTT, pH 7.8 (TSCD). Fractions containing Caspase 3 activity was applied to DEAE Toyopearl 650 M (Supelco Inc) equilibrated with Buffer TSCD. The column was eluted with a linear gradient of 20 mM to 120 mM of Tris Hcl pH 7.8 in TSCD. Caspase 3 was eluted in early of the gradient before the majority of impurities eluted. This partially purified Capase 3 was used for inhibitor screening. All operations were performed at 4° C. and Caspase activity was measured using substrate, DEVD-AMC, and Dynatach Fluolite 1000 plate reader.

Caspase 3 Inhibition Assay

Caspase 3 was assayed at 30 degrees C. in 96-well plates using the fluorogenic tetrapeptide substrate N-acetyl-L-aspartyl-L-glutamyl-L-valyl-L-aspartyl-7-amido-4- methylcoumarin (Ac-DEVD-AMC). The assays were conducted at pH 7.5 in a buffered system containing 25 mM Hepes, 10% sucrose, 0.1% CHAPS, and 1–50 uM DTT. The concentration of substrate was fixed at 10 uM. Fluorescence of the liberated 7-amino-4-methylcoumarin was continuously monitored at 460 nm following excitation at 360 nm.

Compound Testing

Compounds were tested at a single dose of 50 to 100 uM. Activity was monitored as described above over a 30 to 60-minute time period following the simultaneous addition of substrate and inhibitor to enzyme to initiate the reaction. The progress curves thus generated were fit by computer to Eq. 1 in order to assess potency and/or time-dependency:

$$v = \frac{(V_o(1 - e^{-k_{obs}t}))}{k_{obs}} \quad (1)$$

Representative compounds of formula (I) have demonstrated positive inhibitory activity in the above noted assay.

Apoptosis Assay (Jurkat Cells)

Materials: Compounds

Compounds were made as stocks (5–100 mM) in dimethylsulfoxide (DMSO) and diluted in DMSO to provide final concentrations, with DMSO concentrations ranging from 0.1–1%.

Preparation of Cells

Jurkat cells were obtained from American Type Culture Collection and grown in RPMI-1640 media supplemented with 10% fetal bovine serum at 37°, 5% $CO_2$. Cells were seeded in T-flasks at 0.03 to 0.08×$10^6$ cells/ml and used for experiments at 0.5 to 1.0×$10^6$ cells/ml. Other proliferative cells can be used with apoptosis induc ed by anti-fas, camptothecine, cerimide or TNF.

Apoptosis Assay

A method for measuring apoptosis is to quantitate the amount of broken DNA fragments using a fluorescent end-labeling method, a system used in the ApopTag kit from Oncor (Gaithersburg, Md.). In brief, the enzyme terminal deoxynucleotidyl transferase extends the DNA fragments with digoxigenin-containing nucleotides, which are then dected with an antidigoxigenin antibody carring fluorescein to allow dection by fluorescence (494 nm excitation and 523 nm emission). Propidium iodide is used as counter stain to measure total DNA content. Flow cytometic analysis was done on Becton-Dickinson (Rutherfor, N.J.) FACScan instrument using CellQuest software.

Methods of Treatment

For therapeutic use the compounds of the present invention will generally be administered in a standard pharmaceutical composition obtained by admixture with a pharmaceutical carrier or diluent selected with regard to the intended route of administration and standard pharmaceutical practice. For example, they may be administered orally in the form of tablets containing such excipients as starch or lactose, or in capsule, ovules or lozenges either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood. Tie choice of form for administration as well as effective dosages will vary depending, inter alia, on the condition being treated. The choice of mode of administration and dosage is within the skill of the art.

The compounds of the present invention, particularly those noted herein or their pharmaceutically acceptable salts which are active when given orally, can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerin, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule. Preferably the composition is in unit dose form such as a tablet or capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilized and then reconstituted with a suitable solvent just prior to administration.

A typical suppository formulation comprises a compound or a pharmaceutically acceptable salt thereof which is active when administered in this way, with a binding and/or lubricating agent such as polymeric glycols, gelatins or cocoa butter or other low melting vegetable or synthetic waxes or fats.

The pharmaceutically acceptable compounds of the invention will normally be administered to a subject in a daily dosage regimen. For a patient this may be, for example, from about 0.001 to about 100 mg/kg, preferably from about 0.001 to about 10 mg/kg animal body weight. A daily dose, for a larger mammal is preferably from about 1 mg to about 1000 mg, preferably between 1 mg and 500 mg or a pharmaceutically acceptable salt thereof, calculated as the free base, the compound being administered 1 to 4 times per day. Unit dosage forms may contain from about 25 $\mu$g to about 500 mg of the compound.

There are many diseases and conditions in which dysregulation of apoptosis plays an important role. All of these conditions involve undesired, deleterious loss of specific cells with resulting pathological consequences.

Bone remodeling involves the initial resorption by osteoclasts, followed by bone formation by osteoblasts. Recently, there have been a number of reports of apoptotic events occurring during this process. Apoptotic events have been observed in both the bone forming and bone resorbing cells in vitro and indeed at the sites of these remodeling units in vivo.

Apoptosis has been suggested as one of the possible mechanisms of osteoclast disappearance from reversal sites between resorption and formation. TGF-$\beta$1 induces apoptosis (approx. 30%) in osteoclasts of murine bone marrow cultures grown for 6 days in vitro. (Hughes, et al., *J. Bone Min. Res.* 9, S138 (1994)). The anti-resorptive bisphosphonates (clodronate, pamidronate or residronate) promote apoptosis in mouse osteoclasts in vitro and in vivo . (Hughes, et al., supra at S347). M-CSF, which has previously been found to be essential for osteoclast formation can suppress apoptosis, suggesting not only that maintenance of osteoclast populations, but also that formation of these multinucleated cells may be determined by apoptosis events. (Fuller, et al., *J. Bone Min. Res.* 8, S384 (1993); Perkins, et al., *J. Bone Min. Res.* 8, S390 (1993)). Local injections of IL-1 over the calvaria of mice once daily for 3 days induces intense and aggressive remodeling. (Wright, et al., *J. Bone Min. Res.* 9, S174 (1994)). In these studies, 1% of osteoclasts were apoptotic 1 day after treatment, which increased 3 days later to 10%. A high percentage (95%) of these apoptotic osteoclasts were at the reversal site. This data suggests that Caspases are functionally very important in osteoclast apoptosis.

Therefore, one aspect of the present invention is the promotion of apoptosis in osteoclasts as a novel therapy for inhibiting resorption in diseases of excessive bone loss, such as osteoporosis, using compounds of Formula (I) as defined herein.

Apoptosis can been induced by low serum in highly differentiated rat osteoblast-like (Ros 17/2.8) cells (Ihbe, et al., (1994) *J. Bone Min. Res.* 9, S167)). This was associated with a temporal loss of osteoblast phenotype, suggesting that maintenance of lineage specific gene expression and apoptosis are physiologically linked. Fetal rat calvaria derived osteoblasts grown in vitro undergo apoptosis and this is localized to areas of nodule formation as indicated by in situ end-labeling of fragmented DNA. (Lynch, et al., (1994) *J. Bone Min. Res.* 9, S352). It has been shown that the immediate early genes c-fos and c-jun are expressed prior to apoptosis; c-fos and c-jun-Lac Z transgenic mice show constitutive expression of these transcription factors in very few tissues, one of which is bone (Smeyne, et al., 1992) *Neuron.* 8, 13–23; and Morgan, J. (1993) Apoptotic Cell Death: Functions and Mechanisms. Cold Spring Harbor October 13–15th). Apoptosis was observed in these animals in the epiphyseal growth plate and chondrogenic zones as the petula ligament calcifies. Chondrogenic apoptosis has also been observed in PTHRP-less mice and these transgenics exhibit abnormal endochondral bone formation (Lee, et al., (1994) *J. Bone Min. Res.* 9, S159). A very recent paper examined a human osteosarcoma cell line which undergoes spontaneous apoptosis. Using this cell line, LAP-4, but not ICE, could be detected and in vitro apoptosis could be blocked by inhibition or depletion of LAP-4 (Nicholson, et al., (1995) *Nature* 376, 37–43). Thus, apoptosis may play a role in loss of osteoblasts and chondrocytes and inhibition of apoptosis could provide a mechanism to enhance bone formation.

Therefore, another aspect of the present invention is the inhibition of apoptosis as a novel therapy to enhance bone formation using compounds of Formula (I) as defined herein.

Osteoarthritits (OA) is a degenerative disease characterized by progressive erosion of articular cartilage. Chondrocytes are the single cell-type found in articular cartilage and perturbations in metabolism of these cells may be involved in the pathogenesis of OA. Injury to cartilage initiates a specific reparative response which involves an increase in the production of proteoglycan and collagen in an attempt to reestablish normal matrix homeostasis. However, with the progress of the disease, the 3-dimensional collagen network is disrupted and cell death of chondrocytes occurs in OA lesions (Malemud, et al.: Regulation of chondrocytes in osteoarthritis. In: Adolphe, M. ed. Biological Regulation of Chondrocytes. Boca Raton:CRC Press, 1992, 295–319). It has been shown that in OA, chondrocytes adjacent to cartilage defects express high levels of bcl-2 (Erlacher, et al., (1995) *J. of Rheumatology*, 926–931). This represents an attempt to protect chondrocytes from apoptosis induced by the disease process.

Protection of chondrocytes during early degenerative changes in cartilage by inhibition of apoptosis may provide a novel therapeutic approach to this common disease. Therefore, another aspect of the present invention is the inhibition of apoptosis as a novel therapy to treat osteoarthritis, using compounds of Formula (I) as defined herein.

Recent evidence shows that chronic, degenerative conditions of the liver are linked to hepatocellular apoptosis. These conditions include chemical-, infectious- and immune/inflammatory-induced hepatocellular degeneration. Apoptosis of liver cells has been observed in liver degenerative states induced by a variety of chemical agents, including acetaminophen (Ray, et al., (1993) *FASEB. J.* 7, 453–463), cocaine (Cascales, et al., (1994) *Hepatology* 20, 992–1001) and ethanol (Baroni, et al., (1994) *J. Hepatol.* 20, 508–513). Infectious agents and their chemical components that have been shown to induce apoptosis include hepatitis ((Hiramatsu, et al., (1994) *Hepatology* 19, 1354–1359; Mita, et al., (1994) *Biochem. Biophys. Res. Commun.* 204, 468–474)), tumor necrosis factor and endotoxin. (Leist, et al., (1995) *J. Immunol.* 154, 1307–1316; and Decker, K. (1993) *Gastroenterology* 28(S4), 20–25). Stimulation of immune/inflammatory responses by mechanisms such as allograft transplantation and hypoxia followed by reperfusion have been shown to induce apoptosis of hepatocytes (Krams, et al., (1995) *Transplant. Proc.* 27, 466–467). Together, this evidence supports that hepatocellular apoptosis is central to degenerative liver diseases.

Therefore, another aspect of the present invention is the inhibition of apoptosis as a novel therapy to treat degenerative liver diseases, using compounds of Formula (I) as defined herein.

Apoptosis is recognized as a fundamental process within the immune system where cell death shapes the immune system and effects immune functions. Apoptosis also is implicated in viral diseases (e.g AIDS). Recent reports indicate that HIV infection may produce an excess of apoptosis, contributing to the loss of $CD4^+$ T cells. Of additional interest is the observation that APO-1/Fas shares sequence homology with HIV-1 gp120.

Therefore, another aspect of the present invention is the inhibition of apoptosis as a novel therapy to treat viral diseases, using compounds of Formnula (I) as defined herein.

Additional therapeutic directions and other indications in which inhibition of apoptotic cysteine proteases is of therapeutic utility, along with relevant citations in support of the involvement for apoptosis in each indication, are presented below in Table 1.

TABLE 1

| Therapeutic Indications Related to Apoptosis | |
|---|---|
| Indication | Citations |
| Ischemia/reperfusion | Barr et al., (1994) BioTechnology 12, 487–493; Thompson, C. B. (1995) Science 267, 1456–1462 |
| Stroke | Barr et al supra; and Thompson, C., supra |
| Polycystic kidney disease | Barr et al., supra; and Mondain, et al., (1995) ORL J. Otorhinolaryngol. Relat. |

TABLE 1-continued

Therapeutic Indications Related to Apoptosis

| Indication | Citations |
|---|---|
| Glomerulo-nephritis | Spec. 57, 28–32<br>Barr et al., supra |
| Osteoporosis | Lynch et al., (1994) J. Bone Min. Res. 9, S352; Nicholson et al., (1995) Nature 376, 37–43 |
| Erythropoiesis/<br>Aplastic anemia | Thompson, C., supra; Koury et al., (1990) Science 248, 378–381 |
| Chronic liver degeneration | Thompson, C., supra; Mountz et al., 1994) Arthritis Rheum. 37, 1415–1420; Goldin et al., (1993) Am. J. Pathol. 171, 73–76 |
| T-cell death | Thompson, C., supra; Ameison et al., (1995) Trends Cell Biol. 5, 27–32 |
| Osteoarthritis - chondrocytes | Ishizaki et al., (1994) J. Cell Biol. 126, 1069–1077; Blanco et al., (1995) Am. J. Pathol. 146, 75–85 |
| Male pattern baldness | Mondain et al., supra; Seiberg et al., (1995) J. Invest. Dermatol. 104, 78–82; Tamada et al., (1994) Br. J. Dermatol 131, 521–524 |
| Alzheimer's disease | Savill, J., (1994) Eur. J. Clin. Invest. 24, 715–723; Su et al., (1994) Neuroreport 5, 2529–2533; Johnson, E., (1994) Neurobiol. Aging 15 Suppl. 2, S187–S189 |
| Parkinson's disease | Savill, J., supra; Thompson, C., supra |
| Type I diabetes | Barr et al., supra |

The IL-1 and TWF inhibiting effects of compounds of the present invention are determined by the following in vitro assays:

Interleukin-1 (IL-1)

Human peripheral blood monocytes are isolated and purified from either fresh blood preparations, from volunteer donors, or from blood bank buffy coats, according to the procedure of Colotta et al, J Immunol, 132, 936 (1984). These monocytes ($1 \times 10^6$) are plated in 24-well plates at a concentration of 1–2 million/ml per well. The cells are allowed to adhere for 2 hours, after which time non-adherent cells are removed by gentle washing. Test compounds are then added to the cells for about 1 hour before the addition of lipopolysaccharide (50 ng/ml), and the cultures are incubated at 37° C. for an additional 24 hours. At the end of this period, culture supernatants are removed and clarified of cells and all debris. Culture supernatants are then immediately assayed for IL-1 biological activity, either by the method of Simon et al., J. Immunol. Methods, 84, 85, (1985) (based on ability of IL-1 to stimulate a Interleukin 2 producing cell line (EL-4) to secrete IL-2, in concert with A23187 ionophore) or the method of Lee et al., J. ImmunoTherapy, 6 (1), 1–12 (1990) (ELISA assay).

Tumour Necrosis Factor (TNF)

Human peripheral blood monocytes are isolated and purified from either blood bank buffy coats or platelet pheresis residues, according to the procedure of Colotta, R. et al., J Immunol, 132(2), 936 (1984). The monocytes are plated at a density of $1 \times 10^6$ cells/ml medium/well in 24-well multi-dishes. The cells are allowed to adhere for 1 hour after which time the supernatant is aspirated and fresh medium (1 ml, RPMI-1640, Whitaker Biomedical Products, Whitaker, Calif.) containing 1% fetal calf serum plus penicillin and streptomycin (10 units/ml) added. The cells are incubated for 45 minutes in the presence or absence of a test compound at 1 nM–10 mM dose ranges (compounds are solubilized in dimethyl sulfoxide/ethanol, such that the final solvent concentration in the culture medium is 0.5% dimethyl sulfoxide/ 0.5% ethanol). Bacterial lipopoly-saccharide (*E. coli* 055:B5 [LPS] from Sigma Chemicals Co.) is then added (100 ng/ml in 10 ml phosphate buffered saline) and cultures incubated for 16–18 hours at 37° C. in a 5% $CO_2$ incubator. At the end of the incubation period, culture supernatants are removed from the cells, centrifuged at 3000 rpm to remove cell debris. The supernatant is then assayed for TNF activity using either a radio-immuno or an ELISA assay, as described in WO 92/10190 and by Becker et al., J Immunol, 1991, 147, 4307.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound of formula

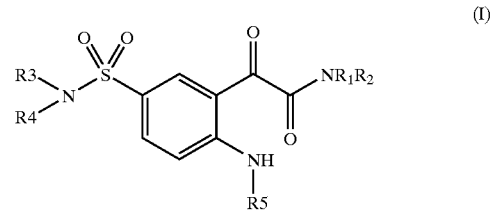

(I)

wherein
   $R_1$ and $R_2$ together with the nitrogen to which they are attached form a 4 to 7 membered ring;
   $R_3$ and $R_4$ together with the nitrogen to which they are attached form a 4 to 7 membered ring;
   $R_5$ is

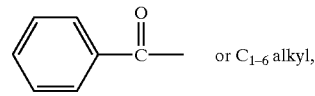 or $C_{1-6}$ alkyl,

2. A compound according to claim 1 wherein $R_5$ is

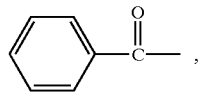,

3. A compound according to claim 1 wherein $R_5$ is methyl.

4. A compound according to claim 1 wherein $R_1$ and $R_2$ are joined to form a 6 membered nitrogen containing ring.

5. A compound according to claim 1 wherein $R_3$ and $R_4$ are joined to form a 6 membered nitrogen containing ring.

6. A compound according to claim 1, selected from the group consisting of:

(S,S)-4-[1-(2-Methoxymethyl)pyrrolidinyl)sulfonyl]-2-[1-(2-methoxymethyl)pyrrolidino-ethanedione]-aniline;
   (S,S)-4-[1-(2-Phenoxymethyl)pyrrolidinyl)sulfonyl]-2-[1-(2-methoxymethyl)pyrrolidino-ethanedione]-aniline;
   (S,S)-4-[1-(2-(Phenoxymethyl)pyrrolidinyl)sulfonyl]-2-[1-(2-methoxymethyl)pyrrolidino-ethanedione]-N-benzoylaniline; and (S,S)-4-[1-(2-(Phenoxymethyl)pyrrolidinyl)sulfonyl]-2-[1-(2-methoxymethyl)pyrrolidino- 1,2-ethanedione]-N-methylaniline.

7. A pharmaceutical composition comprising a compound according to claim 1 and a pharmaceutically acceptable carrier or diluent.

8. A method of blocking excess or inappropriate apoptosis in a mammal in need of such treatment which method comprises administering to said mammal or human an effective amount of a compound according to claim 1, or a pharmaceutically acceptable salt thereof.

9. The method according to claim 8 wherein the excessive or inappropriate apoptosis occurs in Alzheimer disease.

10. The method according to claim 8 wherein the excessive or inappropriate apoptosis occurs in viral infections.

11. The method according to claim 8 wherein the excessive or inappropriate apoptosis occurs during infarction or reperfusion injury.

12. The method according to claim 8 wherein the excessive or inappropriate apoptosis occurs during ischemia.

13. The method according to claim 8 wherein the excessive or inappropriate apoptosis results in excessive bone loss.

14. The method according to claim 8 wherein the excessive or inappropriate apoptosis results in the disease of osteoarthritis.

15. The method according to claim 8 wherein the excessive or inappropriate apoptosis results in hepatocellular degeneration.

16. A method for the treatment of diseases or disorders associated with excessive IL-1β convertase activity, in a mammal in need thereof, which method comprises administering to said mammal an effective amount of a compound according to claim 1, or a pharmaceutically acceptable salt thereof.

17. A method of blocking or decreasing the production of IL-1β and/or TNF, in a mammal in need of such treatment, which method comprises administering to said mammal an effective amount of a compound according to claim 1, or a pharmaceutically acceptable salt thereof.

18. A pharmaceutically acceptable salt of a compound according to claim 1.

19. A pharmaceutical composition comprising a pharmaceutically acceptable salt of a compound according to claim 1 and a pharmaceutically acceptable carrier or diluent.

20. A pharmaceutical composition comprising:
  (a) a pharmaceutically acceptable salt of a compound selected from the group consisting of:
    (S,S)-4-[1-(2-Methoxymethyl)pyrrolidinyl)sulfonyl]-2-[1-(2-methoxymethyl)pyrrolidino-ethanedione]-aniline;
    (S,S)-4-[1-(2-Phenoxymethyl)pyrrolidinyl)sulfonyl]-2-[1-(2-methoxymethyl)pyrrolidino-ethanedione]-aniline;
    (S,S)-4-[1-(2-(Phenoxymethyl)pyrrolidinyl)sulfonyl]-2-[1-(2-methoxymethyl)pyrrolidino-ethanedione]-N-benzoylaniline; and
    (S,S)-4-[1-(2-(Phenoxymethyl)pyrrolidinyl)sulfonyl]-2-[1-(2-methoxymethyl)pyrrolidino-1,2-ethanedione]-N-methylaniline; and
  (b) a pharmaceutically acceptable carrier or diluent.

* * * * *